United States Patent
Vaccaro et al.

(10) Patent No.: US 6,211,182 B1
(45) Date of Patent: Apr. 3, 2001

(54) IMIDAZOLE COMPOUNDS SUBSTITUTED WITH A SIX OR SEVEN MEMBERED HETEROCYCLIC RING CONTAINING TWO NITROGEN ATOMS

(75) Inventors: Wayne Vaccaro, Yardley, PA (US); John J. Piwinski, Clinton Township, NJ (US); Wing C. Tom, Cedar Grove, NJ (US); Daniel M. Solomon, Edison, NJ (US); Robert G. Aslanian, Rockaway, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/264,615

(22) Filed: Mar. 8, 1999

(51) Int. Cl.7 .................... A61K 31/496; C07D 401/14; C07D 403/06; C07D 403/12
(52) U.S. Cl. ................ 514/253.09; 514/254.05; 514/218; 540/575; 544/364; 544/370; 544/337
(58) Field of Search .................... 544/370, 364; 514/252, 253.09, 254.05

(56) References Cited

U.S. PATENT DOCUMENTS

| | | | |
|---|---|---|---|
| 4,767,778 | 8/1988 | Arrang | 514/397 |
| 5,352,707 | 10/1994 | Pompri | 514/651 |
| 5,559,113 | * 9/1996 | Schwartz et al. | 514/252 |

FOREIGN PATENT DOCUMENTS

| | | |
|---|---|---|
| 0420396A2 | 7/1990 | (EP) . |
| WO931812A1 | 2/1993 | (WO) . |
| WO93/12093 | 6/1993 | (WO) . |
| WO95/14007 | 5/1995 | (WO) . |
| 9630343 | * 10/1996 | (WO) . |

OTHER PUBLICATIONS

Howson, et al., *Bioorg. & Med. Chem. Letters*, (1992) vol. 2, pop. 77–78.
van der Goot, et al., *Eur. J. Med. Chem.*, (1992), vol. 27, pp. 511–517.
J. Clapham, et al., *Br. J. of Pharmacol.*, (1993), 65P.
J. Clapham, et al., *J. Psychopharmacol.*, (Abstr. book). A17 (1993).
Yokoyama, et al., *Eur. J. Med. Chem.*, vol. 234 (1993), pp. 129–133.
Schlicker, et al., *Br. J. Pharmacol.*, (1994), vol. 112, pp. 1043–1048.
Leurs, et al., *Progress in Drug Research*, vol. 39 (1992) pp. 127–165.
Lipp, et al., *The Histamine Receptor*, (1992), pp. 57–72.
Bagley, et al., *J. Med. Chem.*, (1991), vol. 34, pp. 827–841.
West, et al., *Molecular Pharmacology*, (1990), pp. 610–613.
Rizzo, et al., *Eur. J. of Pharmacol.*, (1995) vol. 294, pp. 329–335.

* cited by examiner

*Primary Examiner*—Emily Bernhardt
(74) *Attorney, Agent, or Firm*—Palaiyur S. Kalyanaraman

(57) ABSTRACT

This invention discloses novel imidazoles substituted with a six or seven membered heterocyclic ring which contains two nitrogen atoms as part of the heterocyclic ring structure. These compounds have excellent histamine-$H_3$ receptor antagonist activity. Also disclosed are methods for preparing such compounds. In another embodiment, the invention discloses pharmaceutical compositions comprising such imidazoles as well as methods of using them to treat allergy (for example asthma), inflammation, hypertension, raised intraocular pressure (such as glaucoma)—i.e., a method of lowering intraocular pressure, sleeping disorders, states of hyper and hypomotility and acidic secretion of the gastrointestinal tract, hypo and hyperactivity of the central nervous system (for example, agitation and depression) and other CNS disorders (such as Alzheimer's Disease, schizophrenia, and migraine).

An illustrative inventive imidazole is shown below:

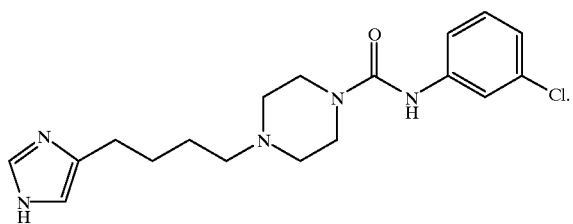

3 Claims, No Drawings

IMIDAZOLE COMPOUNDS SUBSTITUTED WITH A SIX OR SEVEN MEMBERED HETEROCYCLIC RING CONTAINING TWO NITROGEN ATOMS

FIELD OF THE INVENTION

The present invention relates to C- or N-(imidazolylalkyl) substituted cyclic amine compounds having valuable pharmacological properties, especially central nervous system ("CNS") activities and activity against inflammatory disease and allergic conditions. Compounds of this invention are agonists or antagonists of the histamine-$H_3$ receptor.

BACKGROUND OF THE INVENTION $H_3$ receptor sites are known and are of current interest to those skilled in the art as a therapeutic target. U.S. Pat. No. 4,767,778 (Arrang et al) discloses certain imidazoles that behave as agonists of the $H_3$ receptors in rat brain. European Patent Application No. 0 420 396 A2 (Smith Kline & French Laboratories Limited) and Howson et al., (*Bioorg. & Med. Chem. Letters*, (1992), Vol. 2 No. 1, pp. 77–78) describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine-$H_3$ receptor, and these isothiourea analogs of histamine overlap in part with those of the two references cited above. Clapham et al. ["Ability of Histamine-$H_3$ Receptor Antagonists to Improve Cognition and to Increase Acetylcholine Release in vivo in the Rat", *British Assn. for Psychopharmacology*, Jul. 25–28 (1993), reported in *J. Psychopharmacol.* (Abstr. Book), A17] describe the ability of histamine-$H_3$ receptor antagonists to improve cognition and to increase release of acetylcholine in vivo in the rat. Clapham et al. ["Ability of the selective Histamine-$H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of Thioperamide, a Histamine-$H_3$ Receptor Antagonist, on —Electrically Induced Convulsions in Mice", *Eur. J. Pharmacol.*, (1993), Vol. 234, pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-Al (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", *British J. Pharmacol.*, (1994), Vol. 112, 1043–1048] describe a number of imidazolylalkyl compounds wherein the imidazolylalkyl group is bonded to a guanidine group, an ester group, an amide group, a thioamide group and a urea group, and compared these to thioperamide. Leurs et al. ["The Histamine-$H_3$-receptor: A Target for Developing New Drugs", *Progr. Drug Res.* (1992), Vol. 39, pp. 127–165] and Lipp et al. ["Pharmacochemistry of $H_3$-receptors" in *The Histamine Receptor*, eds.: Schwartz and Haas, Wiley-Liss, New York (1992), pp. 57–72] review a variety of synthetic $H_3$ receptor antagonists, and Lipp et al. (ibid.) have proposed the necessary structural requirements for an $H_3$ receptor antagonist.

WO 95/14007 claims $H_3$ receptor antagonists of the formula

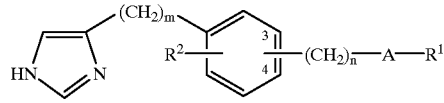

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

Reference is also made to U.S. application, Ser. No. 08/689,951, filed Aug. 16, 1996 which claims the combined use of a histamine-H, receptor antagonist and a histamine-$H_3$ receptor antagonist for treatment of allergy-induced airway responses.

Reference is also made to J. R. Bagley et al, *Journal of Medicinal Chemistry*, (1991), Vol. 34, 827–841, which discloses, among others, N-(imidazolylalkyl) substituted cyclic amine compounds useful as analgesics such as the amine compound with the formula:

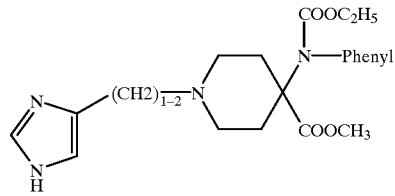

Pending U.S. patent application, Ser. No. 09/173,642, filed Oct. 16, 1998 (R. Wolin et al), discloses N-(imidazolylalkyl) substituted cyclic amine compounds having $H_3$ antagonist activity.

In view of the art's interest in compounds which affect the $H_3$ receptor, novel compounds having agonist or antagonist activity on $H_3$ receptors would be a welcome contribution to the art. This invention provides just such a contribution by providing novel compounds having $H_3$ agonist or antagonist activity.

SUMMARY OF THE INVENTION

This invention provides novel compounds with $H_3$ receptor agonist or antagonist activity with the inventive compound having the general formula depicted in Formula I, including enantiomers, stereoisomers and tautomers thereof, as well as pharmaceutically acceptable salts or solvates of said compounds:

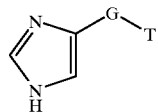

Formula I wherein G is a spacer moiety selected from the group consisting of $C_1$–$C_7$ alkyl, $C_2$–$C_7$ alkenyl, $C_2$–$C_7$ alkynyl, $C_1$–$C_7$ alkyl-NHCO—, and —SO2—, with said alkyl, alkenyl or alkynyl being optionally substituted with one or more groups selected from substituted or unsubstituted alkyl, aryl, aralkyl, alkylaryl, —O—alkyl, and -$CO_2$-alkyl, and wherein said substituents are selected from the group consisting of alkyl, aryl, aralkyl, and halogen; and T is a six-membered ring or a seven-membered ring containing two ring nitrogens and belonging to the formula a shown below, with said T ring being connected to said G moiety at either a ring carbon atom of ring T or a ring nitrogen atom of ring T:

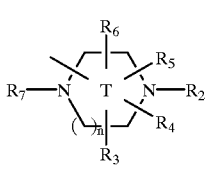

a wherein n is 1 or 2; and $R_2$, $R_3$, $R_4$, $R_5$, $R_6$ and $R_7$ can be the same or different with the proviso that no two of said $R_3$, $R_4$, $R_5$ and $R_6$ can be bound to the same carbon atom of ring T except when at least one of said $R_3$, $R_4$, $R_5$ and $R_6$ is H, wherein said $R_2$, and $R_7$ are independently selected from the group consisting of H, substituted or unsubstituted $C_1$–$C_6$ alkyl, substituted or unsubstituted $C_2$–$C_6$ alkenyl, substituted or unsubstituted $C_2$–$C_6$ alkynyl, aryl, aralkyl, alkylaryl, —C(=O)$R_8$, —$CO_2R_8$, —$SO_2R_8$, S(O)$R_8$, —C(O)$NR_8R_9$, and —C(=$NR_8$)$NR_8R_9$, and said $R_3$, $R_4$, $R_5$, and $R_6$ can be the same or different and are independently selected from the group consisting of H, substituted or unsubstituted $C_1$–$C_6$ alkyl, substituted or unsubstituted $C_2$–$C_6$ alkenyl, substituted or unsubstituted $C_2$–$C_6$ alkynyl, aryl, aralkyl, alkylaryl, — C(=O)$R_8$, —$CO_2R_8$, —$SO_2R_8$, S(O)$R_8$, —C(O)$NR_8R_9$, —C(=$NR_8$)$NR_8R_9$, —C—O—$R_8$, —OC(O)$R_8$, —N($R_8$)$_2$, —$NR_8R_9$, —$SR_8$, —OH, —$OR_8$, —$CH_2OR_8$, —$CH_2N(R_8)_2$, —$CH_2SR_8$, —$NR_8$(CO)$NR_8R_9$, —CX($R_8$)$_2$, —$CX_2R_8$, $CX_3$, —$OCX_3$, —N($R_8$)—S(O)$R_9$, —N($R_8$)—$SO_2R_9$, (=O), (=N—$OR_8$), —$NR_8$—$SO_2$—$NR_8R_9$, —$SO_3H$, and —$PO_3H_2$, wherein $R_8$ and $R_9$ are independently H or substituted or unsubstituted $C_1$–$C_6$ alkyl, substituted or unsubstituted aryl, substituted or unsubstituted aralkyl, substituted or unsubstituted alkylaryl, substituted or unsubstituted alkenylaryl, substituted or unsubstituted alkenyl, heteroaryl and X is a halogen, further wherein when the spacer moiety G is linked to a ring nitrogen atom of ring T then one of said $R_2$ or $R_7$ is absent on the ring nitrogen atom linked to the G moiety and the other of said $R_2$ or $R_7$ is present on the ring nitrogen atom that is not linked to the G moiety, and still further wherein when G is a $C_1$–$C_7$ alkyl and is linked to a ring nitrogen of ring T, then said $R_2$ or $R_7$ on the other ring nitrogen of ring T is not hydrogen, substituted or unsubstituted $C_1$–$C_6$ alkyl or substituted, unsubstituted $C_2$–$C_6$ alkenyl or aryl. The term "substituted" in the phrase "substituted or unsubstituted" refers to appropriate substitution with suitable moieties such as, for example, C1–C6 alkyl, C2–C6 alkenyl, C2–C6 alkynyl, aryl, aralkyl, alkylaryl, cycloalkyl, heterocyclic or halogen.

This invention additionally provides methods for preparing compounds of Formula I.

This invention also provides pharmaceutical compositions comprising a pharmaceutically acceptable carrier and a therapeutically effective amount of a compound of Formula I.

This invention further provides a method of treating allergy, (for example asthma), inflammation, hypertension, raised intraocular pressure (such as glaucoma)—i.e., a method of lowering intraocular pressure, sleeping disorders (e.g., hypersomnia, somnolence, narcolepsy and sleeplessness, such as insomnia), states of hyper and hypomotility and acidic secretion of the gastrointestinal tract, hypo and hyperactivity of the central nervous system (for example, agitation and depression) and other CNS disorders (such as Alzheimer's Disease, schizophrenia, and migraine) comprising administering an effective amount of a composition comprising a compound of Formula I to a patient in need of such treatment.

The invention also covers the aspect of using a compound of Formula I for the treatment of upper respiratory tract disorders.

The invention also covers the aspect of using a compound of Formula I in combination or admixture with an Hi receptor antagonist for the treatment of upper respiratory tract disorders.

DETAILED DESCRIPTION OF THE INVENTION

As used herein the following terms have the following meanings unless indicated otherwise:

alkyl—represents a straight or branched, saturated hydrocarbon chain having from 1 to 6 carbon atoms;

cycloalkyl—represents a saturated carbocyclic ring having from 3 to 6 carbon atoms;

halogen (halo)—represents fluoro, chloro, bromo or iodo;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 $R_9$ groups, each independently selected from halo, alkyl, hydroxy, loweralkoxy, phenoxy, amino, loweralkylamino, diloweralkylamino, polyhaloloweralkyl, and polyhaloloweralkoxy. Preferred aryl groups include phenyl and substituted phenyl, 1-naphthyl, 2-naphthyl and indanyl;

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6 or 7-membered and may or may not have double bonds that lack delocalized pi electrons, which ring structure has from 2 to 8, preferably from 3 to 6 carbon atoms; e.g., 2- or 3-piperidinyl, 2- or 3-piperazinyl, 2- or 3-morpholinyl, or 2- or 3-thiomorpholinyl;

heteroaryl—represents a cyclic organic group having at least one O, S and/or N atom interrupting a carbocyclic ring structure and having a sufficient number of delocalized π-electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl;

DMF—N, N,-dimethylformamide
SEM—2-(trimethylsilyl)ethoxymethyl
THF—tetrahydrofuran
DBU=1,8-diazabicyclo[5.4.0]undec-7-ene
DBN=1,5-diazabicyclo[4.3.0]non-5-ene
EDCI=1-(3-Dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
$NaBH(OAc)_3$=sodium triacetoxyborohydride
LDA=lithium diisopropylamide
p-TsOH=p-toluenesulfonic acid
TMAD=N, N, N', N'-tetramethylazodicarboxamide
CSA =camphorsulfonic acid
NMM=N-methylmorpholine
DCE=dichloroethane One preferred group of compounds within Formula I has the general Formula II:

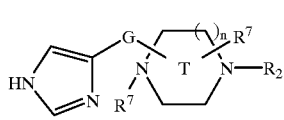

Formula II wherein the symbols are as defined for Formula I.

Of particular interest within this group are compounds of Formula II wherein n is 1. The preferred meaning of $R_2$ is

—Y—$(CH_2)_p$—$R_6$ wherein Y is a bond or —CO— or —$SO_2$—, p is 0 or 1 and $R_6$ is mono- or di-substituted or unsubstituted phenyl. When a group $R_7$ is present, each $R_7$ independently represents hydrogen, benzyl or a group as defined for $R_2$ above, wherein $R_2$ and $R_7$ may be the same or different. Preferably the group $R_7$ that is not attached to the nitrogen is hydrogen. The substituents on the phenyl ring are preferably chlorine.

A second preferred group of compounds within Formula I has the general Formula IIA:

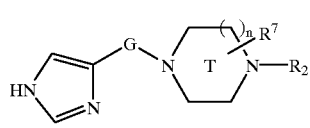

Formula IIA wherein the symbols are as defined for Formula I.

Of particular interest within this group are compounds of Formula IIA wherein n is 1 and G is $C_1$–$C_7$ alkyl.

Certain compounds of the invention may exist in different isomeric (e.g., enantiomers and diastereoisomers) forms. The invention contemplates all such isomers both in pure form and in admixture, including racemic mixtures. Enol forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Certain basic compounds of the invention also form pharmaceutically acceptable salts, e.g., acid addition salts.

For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate.

The free base forms differ from their respective salt forms somewhat in certain physical properties, such as solubility in polar solvents, but the acid and base salts are otherwise equivalent to their respective free base forms for purposes of the invention. All such acid and base salts are intended to be pharmaceutically acceptable salts within the scope of the invention and all acid and base salts are considered equivalent to the free forms of the corresponding compounds for purposes of the invention.

General Preparation Schemes:

The compounds of this invention may be prepared according to suitable processes known in the art for making similar compounds, e.g. processes described in the literature referred to above. Unless stated otherwise, reactions are conducted at an appropriate temperature which allows the reaction to proceed at a reasonable rate to completion.

The basic principle for producing the compounds of this invention comprises first preparing a compound of Formula III:

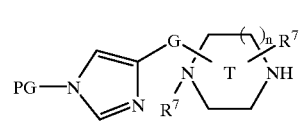

Formula III or compound of Formula IV:

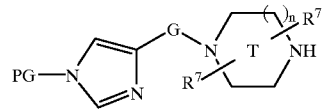

Formula IV wherein PG is a protecting group. As can be seen, compounds of Formulas III and IV differ in whether G is connected to a ring carbon (Formula III) or ring nitrogen (Formula IV) of ring T. Compounds of Formula III and of Formula IV may then be reacted with a compound which introduces the desired group $R_2$ (and, if appropriate and desired, a group $R_7$) followed by removal of the protecting group using suitable methods. The compounds of Formulas III and IV may be either known or may be obtained by standard processes well known in the art, or prepared as described below.

The selection of starting compounds for making compounds of Formulas III and IV generally depends on the meaning of G. The following schemes illustrate the preparation of compounds of Formula III:

Preparation of Compounds of formula III (Reaction Scheme 1):

Scheme 1

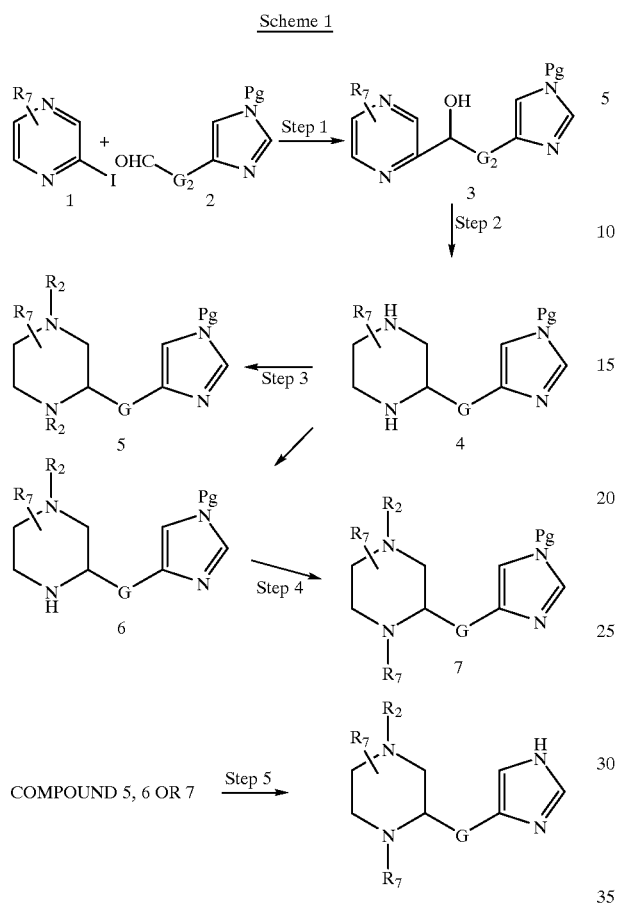

In the above formulas, $G_2$ is a group G with one carbon atom less, and Pg is a suitable protecting group such as, for example, triphenylmethyl ("trityl") or 2-(trimethylsilyl)ethoxymethyl.

In Scheme 1, in step 1, compound 1 is dissolved in an organic solvent such as, for example, tetrahydrofuran, and treated with a base such as, for example, n-butyllithium. Subsequently, an aldehyde 2 is added and compound 3 is obtained. In step 2, compound 3 is dissolved in a suitable alcohol such as, for example, ethanol and hydrogenated under pressure (16–60 psi) in the presence of an appropriate catalyst such as, for example, platinum oxide to provide compound 4. In step 3, compound 4 is suitably reacted with $R_2$ L (where L is a leaving group such as Cl, Br, I, OH or activated versions of OH like $OSO_2CF_3$ generated independently or in situ) to place $R_2$ on the indicated nitrogen to produce compounds 5 and 6. The ratios of 5 and 6 can be varied by the amount of $R_2L$ employed. The reactions may be conducted in the appropriate solvents including, for example, ether, tetrahydrofuran, dioxane, dimethylsulfoxide, dimethylformamide, water, methylene chloride, toluene, with or without the presence of a suitable base such as, for example, triethylamine or lithium diisopropylamide or sodium hydride, at temperatures ranging from −78° to 200° C. Additionally compound 4 can be treated with, for example, trimethylaluminum in solvents such as toluene of tetrahydrofuran, prior to the addition of $R_2L$ where $R_2L$ is $RCO_2R''$ and R" is a lower alkyl such as ethyl to provide compounds 5 and 6 where $R_2$ is $—CO—(CH_2)_pR_6$.

In step 4, compound 5 is reacted with $R_7L$ to place $R_7$ on the indicated nitrogen to produce compound 7. L is a leaving group as defined above and the reactions may be carried out under conditions as outlined above. Deprotection of compounds 5, 6 and 7 may be carried out using standard procedures well known in the art. For example, if Pg is trityl, treatment with dilute aqueous acid such as, for example HCl or HBr, at temperatures of about 25° to 100° C. provides the final compounds.

Alternatively, compounds of Formula III wherein G is $—CH_2CH_2—$ may be obtained by reaction Scheme 2:

Scheme 2

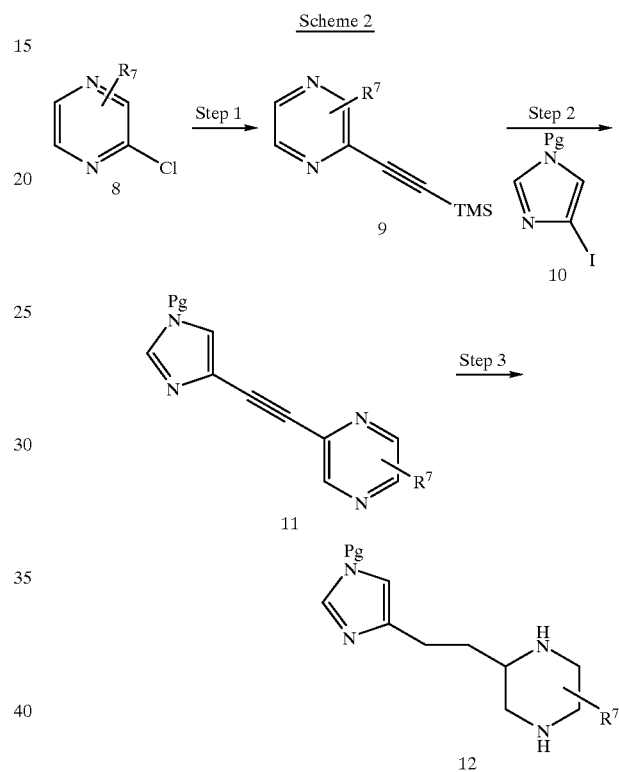

In Scheme 2, in step 1, compound 8, is dissolved in a suitable solvent such as, for example, diisopropylamine. Trimethylsilylacetylene, dichlorobis(triphenylphosphine)palladium chloride and copper iodide are added and allowed to react at temperatures between 25° and 60° C. to provide compound 9.

In step 2, compound 9 and compound 10 are dissolved in a suitable organic solvent such as, for example, dimethylformamide, and treated with a base such as potassium acetate, and a catalyst such as tetrakis-(triphenylphosphine)palladium at temperatures between 25 and 200° C. to afford compound 11.

In step 3, compound 11 is dissolved in a suitable organic solvent such as ethanol and hydrogenated under pressure (16–60 psi) in the presence of an appropriate catalyst such as platinum oxide to provide compound 12.

Compounds of Formula IV where G is linked to a nitrogen atom of ring T may be prepared as outlined in Scheme 3:

Scheme 3

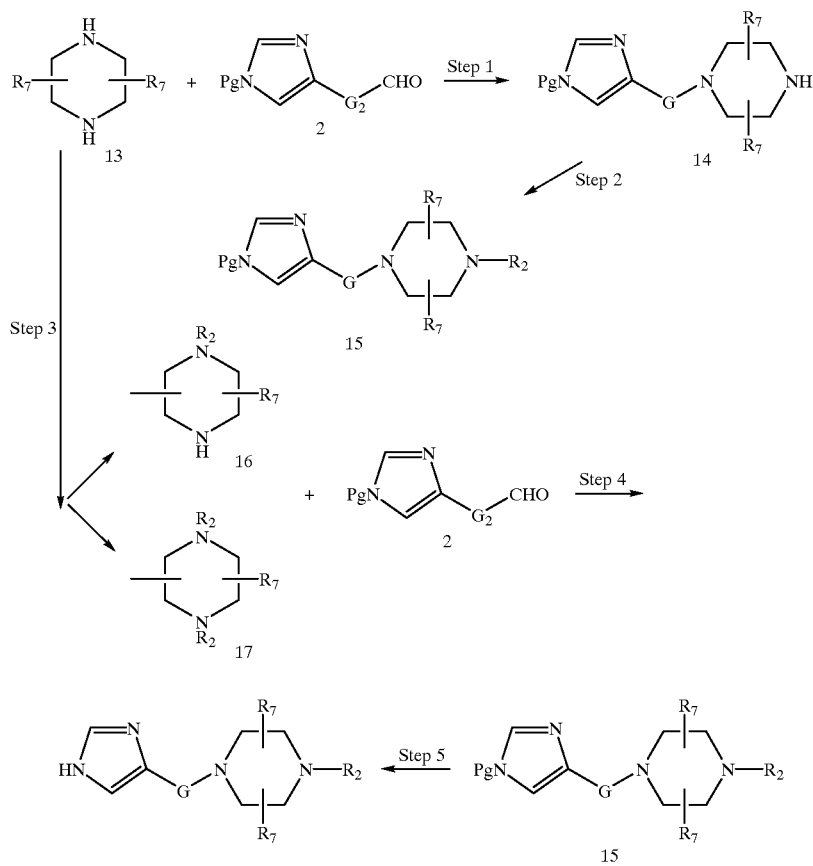

In Scheme 3, in step 1, compound 13 is reacted with an aldehyde of structure 2, where Pg represents a protecting group such as triphenylmethyl, 2-(trimethylsilyl)ethoxymethyl and the like, under standard reductive amination conditions such as, for example, treatment with sodium triacetoxyborohydride in acetic acid to provide compound 14.

In step 2, compound 14 is reacted with $R_2L$ to place $R_2$ on the indicated nitrogen to produce compound 15. L is a leaving group such as Cl, Br, I, OH or activated versions of hydroxyl such as, for example, $OSO_2CF_3$ generated independently or in situ. The reaction may be conducted in an appropriate solvent or solvents including, for example, ether, tetrahydrofuran, dioxane, dimethylsulfoxide, dimethylformamide, water, methylene chloride, toluene with or without the presence of a suitable base such as triethylamine or lithium diisopropylamide or sodium hydride at temperatures ranging from −78° to 200° C.

Compound 15 is then deprotected according to standard procedures as outlined above.

Alternatively one may proceed as follows: In step 3, compound 13 is reacted with $R_2L$ to place $R_2$ on the indicated nitrogens to produce compounds 16 and 17. The ratio of compounds 16 and 17 may be varied by the amount of $R_2$ L employed. L is as defined above. The reaction conditions outlined above may be applied.

In step 4, compound 16 is reacted with an aldehyde of structure 2, under standard reductive amination conditions such as treatment with sodium triacetoxyborohydride in acetic acid to provide compound 15. Deprotection of 15 provides a compound of this invention.

Compounds of Formula III may also be synthesized by the methods outlined in Scheme 4:

Scheme 4

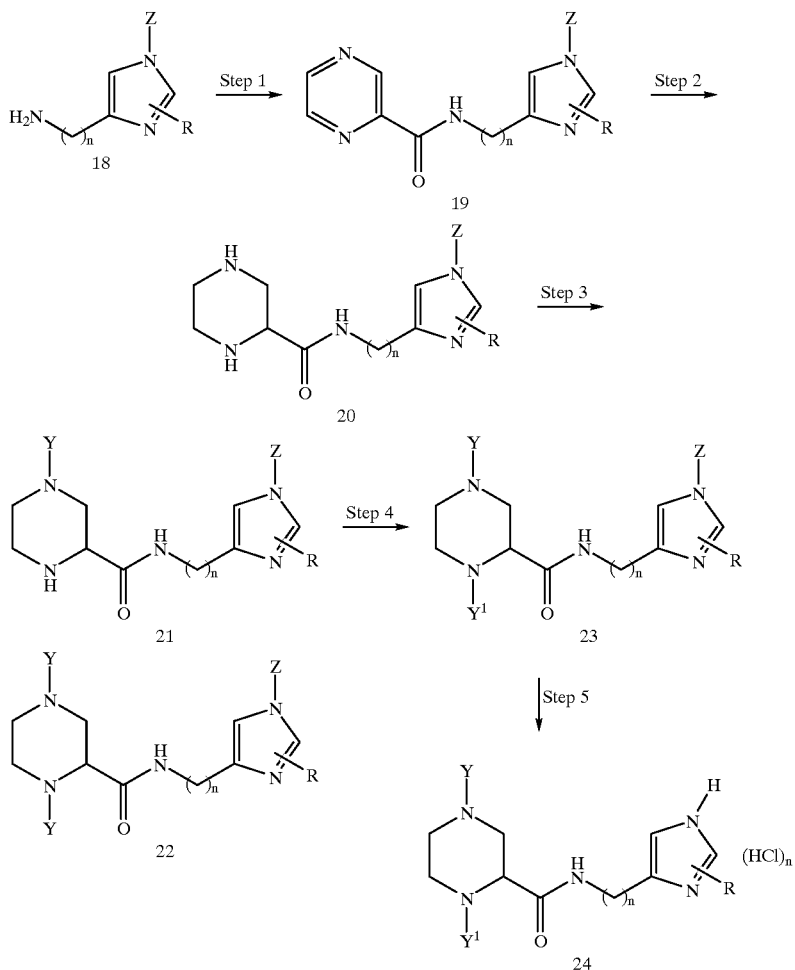

In Scheme 4, step 1, compound 18, where R is hydrogen, alkyl or aryl and n=1–10, Z represents a protecting group such as triphenylmethyl, 2-(trimethylsilyl)ethoxymethyl and the like, was condensed with pyrazinecarboxylic acid under standard amidation conditions such as 1-3 (dimethylaminopropyl)-3-ethylcarbodiimide hydrochloride, hydroxybenzotriazole and N-methylmorpholine in organic solvents such as dimethylformamide and methylene chloride to provide compound 19.

In step 2, compound 19 is dissolved in an organic solvent such as methylene chloride and diluted with an alcohol like methanol. Hydrogenation of 19 at pressures ranging between 16 and 60 psi in the presence of a suitable catalyst such as platinum oxide affords compound 20.

In step 3, compound 20 is reacted with Y-L to place Y on the indicated nitrogen to produce compounds 21 and 22. The ratios of 21 and 22 can be varied by the amount of Y-L employed. Y can be $VXR_1$ where V can be chosen from CO, $CO_2$, $CH_2$, $SO_2$, X can be $(CH_2)_{0-10}$, and $R_1$ can be chosen from the group consisting of hydrogen, alkyl, cycloalkyl, benzyl, substituted benzyl, allyl, aryl, substituted aryl, heteroaryl or propargyl. L is a leaving group such as Cl, Br, I, OH and activated versions of OH like $OSO_2CF_3$ generated independently or in situ. The reactions may be conducted in the appropriate solvents including ether, tetrahydrofuran, dioxane, dimethylsulfoxide, dimethylformamide, water, methylene chloride, toluene with or without the presence of a suitable bases such as triethylamine or lithium diisopropylamide or sodium hydride at temperatures ranging from −78 to 200° C. Additionally compound 20 can be treated with trimethylaluminum in solvents such as toluene or tetrahydrofuran prior to the addition of Y-L where Y-L is $RCO_2R''$ and $R''$ is lower alkyl such as ethyl to provide compounds 21 and 22 Y is COR. Compound 20 may also be reacted with aldehydes of structure $R_1CHO$ under standard reductive amination conditions such as treatment with sodium triacetoxyborohydride in acetic acid to provide compounds 21 and 22 where Y is $CH_2R_1$. The ratio of 21 and 22 can be varied by the amount of $R_1CHO$ employed.

In step 4, compound 21 is reacted with $Y^1$-L to place $Y^1$ on the indicated nitrogens to produce compound 23. $Y^1$ can be $VXR_1$ where V can be chosen from CO, $CO_2$, $CH_2$, $SO_2$, X can be chosen from $(CH_2)_{0-10}$, CO, $CO_2$, $SO_2$, SO, S, O, N, $NR_1$ and $R_1$ can be chosen from the group consisting of hydrogen, alkyl, cycloalkyl, benzyl, substituted benzyl, allyl, aryl, substituted aryl, heteroaryl or propargyl. L is a leaving group such as Cl, Br, I, OH and activated versions of OH like $OSO_2CF_3$ generated independently or in situ. The reactions may be conducted in the appropriate solvents including ether, tetrahydrofuran, dioxane, dimethylsulfoxide, dimethylformamide, water, methylene chloride, toluene with or without the presence of a suitable bases such as triethylamine or lithium diisopropylamide or sodium hydride at temperatures ranging from −78° to 200° C. Additionally compound 23 can be treated with trimethylaluminum in solvents such as toluene or tetrahydrofuran prior to the addition of $Y^1$-L where $Y^1$-L is $RCO_2R''$ and $R''$ is lower alkyl such as ethyl to provide compound 23 where $Y^1$ is COR. Compound 21 may also be reacted with aldehydes of structure $R_1CHO$ under standard reductive amination conditions such as treatment with sodium triacetoxyborohydride in acetic acid to provide compound 23 where $Y^1$ is $CH_2R_1$.

In step 5, when Z is triphenylmethyl, compound 23 is deprotected by treatment with dilute aqueous acid such as HCl or HBr at a temperature of about 25° to 100° C. to produce compound 24. In a similar manner compounds 19, 20, 21 and 22 can be deprotected. Other protecting groups are removed by methods well known in the art.

The thus prepared compounds may be analyzed for their composition and purity as well as characterized by standard analytical techniques such as, for example, elemental analysis, NMR, mass spectroscopy, and IR spectra.

The inventive compounds can readily be evaluated to determine activity at $H_3$ receptors by known methods, including, for example, the guinea pig brain membrane assay and the guinea pig neuronal ileum contraction assay, both of which are described in U.S. Pat. No. 5,352,707. Another useful assay utilizes rat brain membranes and is described by West et al, ("Identification of Two $H_3$-Histamine Receptor Subtypes", *Molecular Pharmacology*, (1990), Vol. 33, 610–613. Several of the present compounds were found to have high $H_3$ antagonist activity.

In another embodiment, this invention provides pharmaceutical compositions comprising the inventive imidazolylalkyl compounds as an active ingredient. The pharmaceutical compositions generally additionally comprise a pharmaceutically acceptable carrier diluent, excipient or carrier (collectively referred to herein as carrier materials). Because of their $H_3$ antagonist activity, such pharmaceutical compositions possess utility in treating allergy, inflammation, nasal congestion, hypertension, glaucoma, sleeping disorders, states of hyper- and hypo-motility of the gastrointestinal tract, hypo- and hyperactivity of the central nervous system, Alzheimer's Disease, schizophrenia, migraines and the like diseases.

In yet another embodiment, the present invention discloses methods for preparing pharmaceutical compositions comprising the inventive imidazolylalkyl compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day. The amount and frequency of the administration will be regulated according to the judgment of the attending clinician. A generally recommended daily dosage regimen for oral administration may range from about 0.04 milligrams to about 4,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels-refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures.

The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and dl-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform.

Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hyper- and hypomotility of the gastrointestinal tract, hypo- and hyperactivity of the central nervous system, Alzheimer's Disease, schizophrenia, migraines and the like. The method comprises administering a therapeutically effective amount of the inventive pharmaceutical composition to a patient having such a diseases or diseases and in need of such a treatment.

In a still another embodiment, this invention discloses pharmaceutical compositions comprising the inventive imidazolylalkyl compounds in combination with one or more histamine-$H_1$ receptor antagonists. Optionally there may be a suitable pharmaceutically acceptable carrier present. Numerous chemical substances are known to have histamine-$H_1$ receptor antagonist activity. Many such compounds can be classified broadly as ethanolamines, ethylenediamines, alkylamines, phenothiazines, piperidines, and the like. Illustrative Hi receptor antagonists useful in the practice of the present invention include, without limitation, astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as desloratadine or "DCL"), doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine, and tripolidine.

Other compounds can readily be evaluated to determine activity at $H_1$ receptors by known methods including, for example, specific blockade of the contractile response to histamine of isolated guinea pig ileum. All such $H_1$ receptor antagonists are suitable to prepare the pharmaceutical compositions.

Yet another embodiment of the invention discloses methods for preparing pharmaceutical compositions comprising the inventive imidazolylalkyl compounds and one or more histamine-$H_1$ receptor antagonists. And a still another embodiment discloses the aspect of using such compositions for treatment of allergy-induced airway (e.g. upper airway) responses. Those skilled in the art will realize that the term "upper airway" means the upper respiratory system—i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following Examples are being provided to further illustrate the present invention. They are for illustrative purposes only; the scope of the invention is not to be considered limited in any way thereby. Reasonable modifications and alterations are presumed to be within the spirit and scope of the invention.

EXAMPLES

Example 1

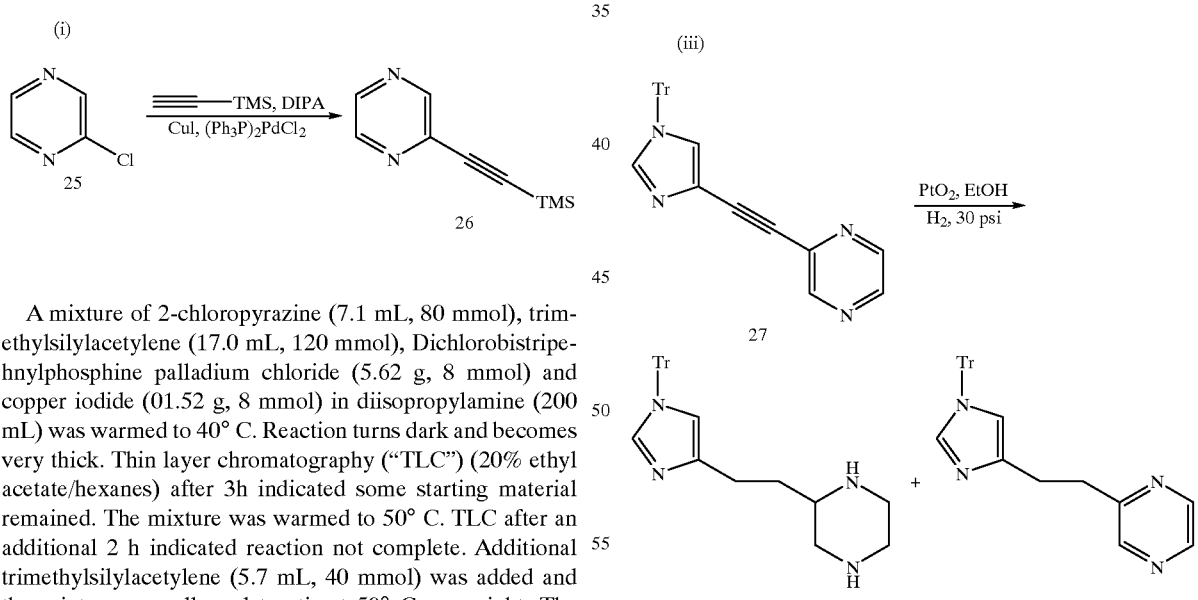

A mixture of 2-chloropyrazine (7.1 mL, 80 mmol), trimethylsilylacetylene (17.0 mL, 120 mmol), Dichlorobistripehnylphosphine palladium chloride (5.62 g, 8 mmol) and copper iodide (01.52 g, 8 mmol) in diisopropylamine (200 mL) was warmed to 40° C. Reaction turns dark and becomes very thick. Thin layer chromatography ("TLC") (20% ethyl acetate/hexanes) after 3h indicated some starting material remained. The mixture was warmed to 50° C. TLC after an additional 2 h indicated reaction not complete. Additional trimethylsilylacetylene (5.7 mL, 40 mmol) was added and the mixture was allowed to stir at 50° C. overnight. The mixture was cooled to room temperature and filtered through celite. The filter cake was well washed with ethyl acetate until TLC of the filtrate indicated all of the desired product had eluted. The filtrate was concentrated onto enough silica gel such that a free-flowing powder was obtained. The powder was loaded onto a chromatography column prepacked with 5% ethyl acetate/hexanes. Elution with 5% ethyl acetate/hexanes followed by 10% ethyl acetate/hexanes provided 13.4 g (95%) of 26 as a dark oil.

A mixture of the 26 (3.68 g, 21 mmol), 4-iodo-1-triphenylmethyl-imidazole (10.1 g, 23 mmol), potassium acetate (3.1 g, 31.5 mmol) and tetrakistriphenylphosphine palladium (1.99 g, 2.1 mmol) was warmed to 100° C. TLC (20% ethyl acetate/hexanes) indicated consumption of starting material. The mixture was cooled to room temperature and filtered through celite. The filter cake was well washed with ethyl acetate. The filtrate was concentrated onto enough silica gel such that a free-flowing powder was obtained. The powder was loaded onto a chromatography column prepacked with 20% ethyl acetate/hexanes. Elution with the same solvent provided 3.7 g (93%) of 27 as an oil.

27 (7.2 g, 17.4 mmol) was dissolved in ethanol (500 mL) and purged with nitrogen. Platinum oxide (0.71 g, 3.1 mmol) was added and the resulting mixture was hydrogenated on a Parr apparatus at 30 psi. TLC (20% Methanol/methylene chloride) indicated that although the starting material had been consumed, multiple products were visible. Additional platinum oxide (1 g, 4.4 mmol) was added and the mixture was hydrogenated on a Parr apparatus at 30 psi overnight.

The mixture was filtered through celite and the filter cake was washed well with ethanol. The filtrate was concentrated onto enough silica gel such that a free-flowing powder was obtained. The powder was loaded onto a silica gel chromatography column prepacked with 10% methanol/methylene chloride. Elution with 10% methanol/methylene chloride followed by 5% ammonium hydroxide (conc.)/10% methanol/methylene chloride provided 5.1 g (69%) of 28 as an amber oil and impure 29. Compound 29 was rechromatographed with 100% ethyl acetate followed by 5% triethylamine/ethyl acetate to provide 0.56 g (8%) of pure 29 as a clear oil.

(iv)

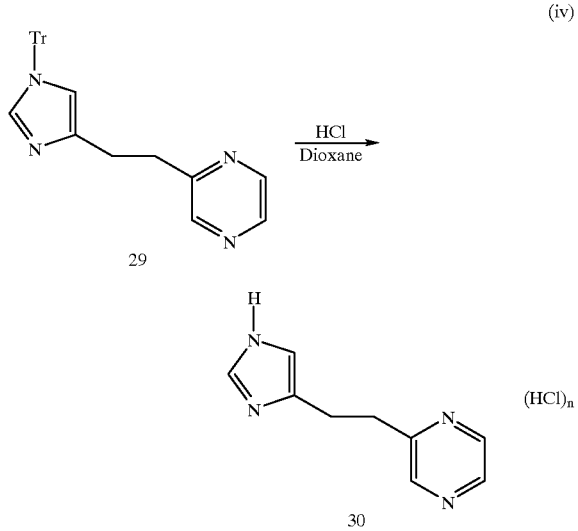

29 (0.51 g, 1.22 mmol) was dissolved in HCl (30 mL, 4M in dioxane) and heated to 60° C. overnight. A precipitate formed. The mixture was cooled to room temperature and the precipitate was collected by vacuum filtration, washed with ethyl acetate and dried to give 0.233 g (67%) of 30 as an amber solid.

Example 2

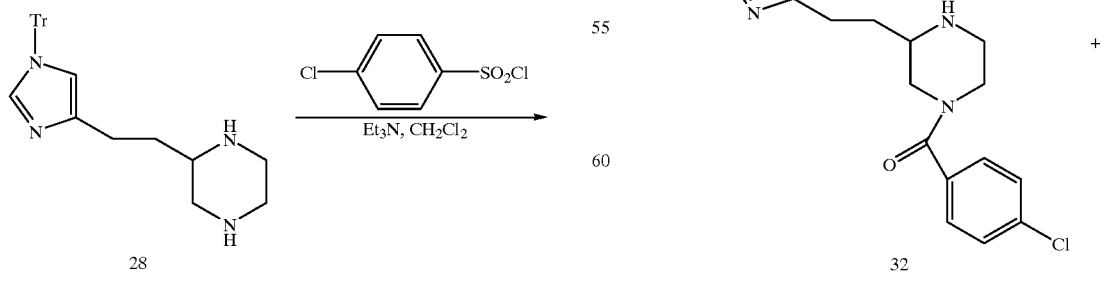

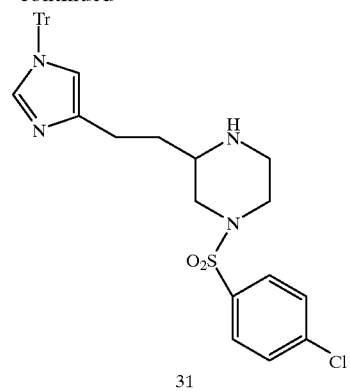

4-chlorobenzenesulfonyl chloride (0.24 g, 1.1 mmol) was added to a room temperature solution of 28 (0.54 g, 1.3 mmol) and triethylamine (0.27 ml, 1.9 mmol) in methylene chloride (5 mL). The resulting mixture was stirred overnight. TLC (5% Methanol/ethyl acetate) indicated starting material was consumed. The reaction mixture was concentrated onto enough silica gel such that a free-flowing powder was obtained. The powder was loaded onto a silica gel chromatography column prepacked with 5% methanol/ethyl acetate. Elution with 5% methanol/methylene chloride followed by 10% methanol/methylene chloride provided 0.63 g (93%) of pure 31 as a white foam.

Deprotection according to the process described above provided the desired compound.

Example 3

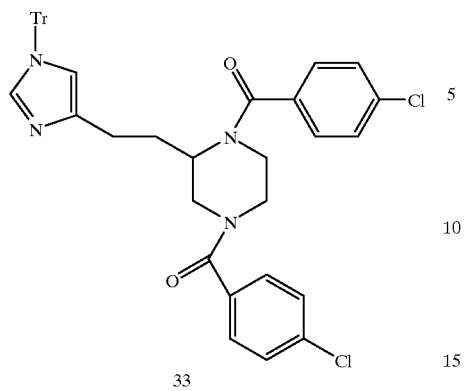

33

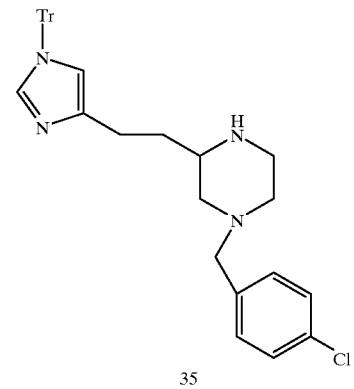

35

1-3-(Dimethylaminopropyl)-3-ethylcarbodiimide hydrochloride (0.94 g, 3.2 mmol) was added to a room temperature solution of 28 (1.0 g, 2.4 mmol), 4-chlorobenzoic acid (0.38 g, 2.4 mmol), N-methylmorpholine (0.8 mL, 7.3 mmol) and hydroxybenzotriazole (0.4 g, 2.9 mmol) in dimethylformamide (6 mL) and methylene chloride (3 mL). The resulting mixture was stirred overnight. TLC (10% methanol/methylene chloride) indicated consumption of starting material. The mixture was transferred to a separatory funnel, diluted with ethyl acetate, washed with water and brine, dried over anhydrous sodium sulfate, filtered and concentrated onto enough silica gel such that a free-flowing powder was obtained. The resulting powder was loaded onto a chromatography column prepacked with silica and 10% methanol/methylene chloride. Elution with 10% methanol/methylene chloride followed by 5% ammonium hydroxide (conc.)/10% methanol/85% methylene chloride gave 0.89 g (65%) of 32 and 0.25 g (15%) of 33. Deprotection provided the corresponding deprotected compound.

Triacetoxyborohydride (0.72 g, 3.4 mmol) was added to a room temperature solution of 28 (1.0 g, 2.4 mmol) and 4-Chlorobenzaldehyde (0.34 g, 2.4 mmol) in dichloroethane (6 mL). The resulting mixture was stirred overnight. The mixture was quenched with saturated sodium bicarbonate and rapidly stirred for 2 hours. The mixture was transferred to a separatory funnel, diluted with methylene chloride, washed with water and brine, dried over anhydrous sodium sulfate, filtered and concentrated onto enough silica gel such that a free-flowing powder was obtained. The resulting powder was loaded onto a chromatography column prepacked with silica and 10% methanol/methylene chloride. Elution with 10% methanol/methylene chloride followed by 5% ammonium hydroxide (conc.)/10% methanol/85% methylene chloride gave 0.22 g (14%) of 34 and 0.82 g (62%) of 35. Deprotection provides the corresponding deprotected compounds.

Example 5

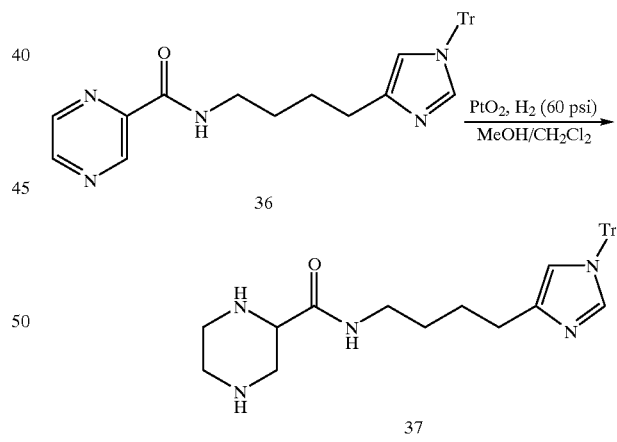

36 (4.71 g, 9.7 mmol) was dissolved in methylene chloride (50 mL), diluted with ethanol (100 mL) and purged with nitrogen. Platinum oxide (0.47 g) was added and the mixture was hydrogenated overnight on a Parr apparatus at 60 psi. TLC (10% methanol/methylene chloride) indicated consumption of starting material. The mixture was filtered through celite and the filter cake was well washed with methanol. The filtrate was concentrated onto enough silica gel such that a free-flowing powder was obtained. The resulting powder was loaded onto a chromatography column prepacked with silica and 10% methanol/methylene chlo- Example 4

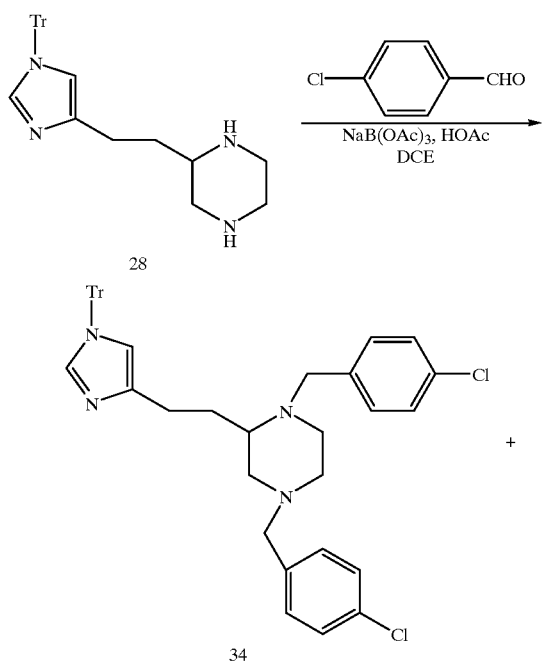

ride. Elution with 10% methanol/methylene chloride followed by 5% ammonium hydroxide (conc.)/10% methanol/methylene chloride provided 4.24 g (89%) of 37 as an oil. Deprotection provides the corresponding deprotected compounds.

Example 6

Steps 1 and 2:

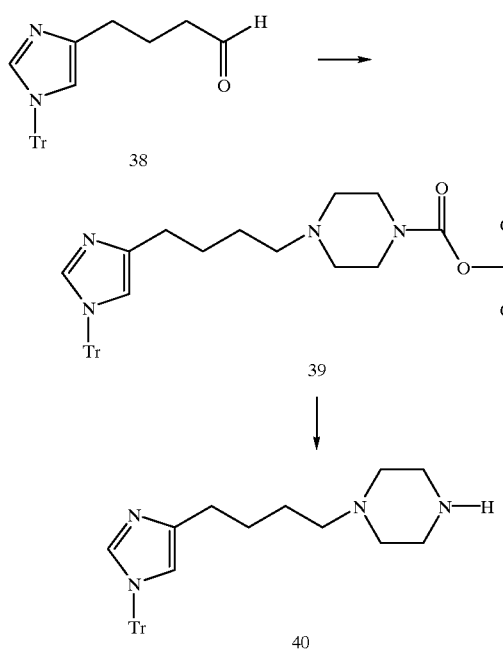

To a stirred solution of the 4-carbon aldehyde 38 (13.3 g, 35 mmol) and tert-butyl-1-piperazinecarboxylate (6.5 g, 35 mmol) in 130 ml of 2,2,2-trifluoroethanol was added 13 g of molecular sieve "3A" followed by portionwise addition of sodium cyanoborohydride (2.2 g, 35 mmol). The mixture was stirred at ambient temperature for two days and then concentrated. The residue was taken up in ethyl acetate, washed successively with dilute sodium carbonate, brine, and concentrated. The residue was chromatographed on SiO2 eluting with MeOH/CH$_2$Cl$_2$ (1:9) to afford 12.4 g (65%) of product 39 as a glass. FAB-MS m/z 551 (MH+).

A solution of 39 (3.7 g, 6.9 mmol) in 20 ml of methanol and 20 ml of 8.7% anhydrous hydrochloric acid/ether solution was stirred at ambient temperature for 18 h. and concentrated. The residue was basified with dilute sodium hydroxide and extracted with ethyl acetate. Concentration of the ethyl acetate solution resulted in 2.8 g of viscous residue which was purified by flash chromatography on SiO$_2$ eluting with CH$_2$Cl$_2$—MeOH-28% NH$_4$OH (90:8:1) to afford 0.9 g of 40 as a syrup. FAB-MS m/z 451 (MH+).

Steps 3 and 4:

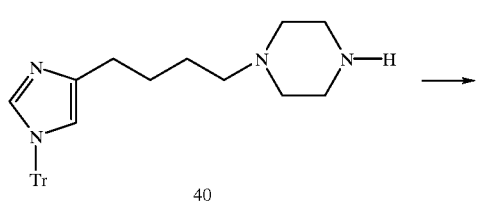

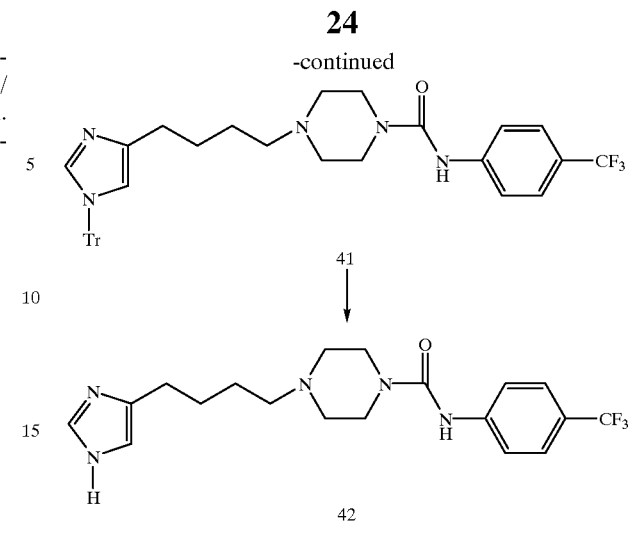

To a stirred solution of 40 (0.6 g, 1.33 mmol) in 20 ml of THF-ether (1:2) was added 4-trifluoromethylphenyl isocyanate (0.33 g, 1.75 mmol). The mixture was stirred at ambient temperature for 2 h and concentrated. The residue was chromatographed on SiO$_2$ eluting with 10% MeOH in CH$_2$Cl$_2$ to produce 0.6 g of gummy product 41. FAB-MS m/z 638 (MH+).

A solution of 41 (0.55 g, 0.86 mmol) and maleic acid (0.22 g, 1.89 mmol) in 20 ml of 90% MeOH was refluxed for 1 h. The mixture was concentrated and the solid residue triturated with ethyl acetate and filtered to afford 0.47 g (mp 175–180° C.) of 42 dimaleate. FAB-MS m/z 396 (MH+). Anal. (C$_{19}$H$_{24}$F$_3$N$_5$O.2C$_4$H$_4$O$_4$) C, H, N.

Example 7

Steps 1 and 2:

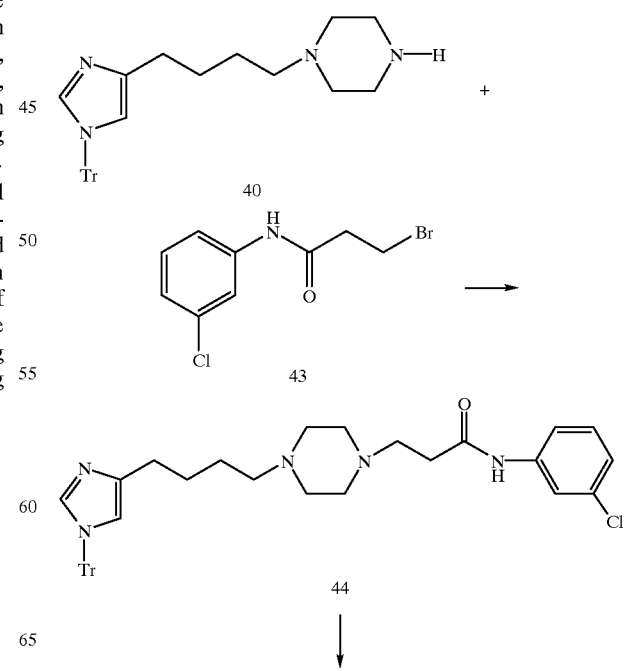

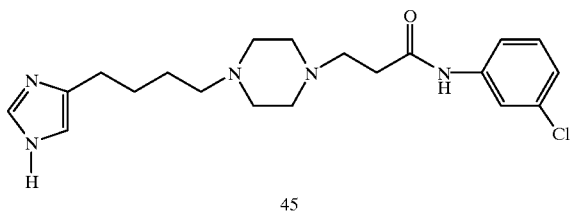

45

To a stirred suspension of 60% sodium hydride in oil dispersion (0.18 g, 4.4 mmol) in 20 ml of anhydrous DMF at 0° C. was added 0.6 g (1 mmol) of 40 trihydrochloride, followed by a solution of 43 (0.29 g, 1.1 mmol) in 10 ml of DMF. The mixture was warmed at 50° C. for 18 h and poured into ice water (30 ml). Extraction with methylene chloride and subsequent concentration gave a viscous residue which was chromatographed on $SiO_2$ eluting with 8% MeOH in $CH_2Cl_2$ to produce 0.33 g of gummy product 44. FAB-MS m/z 632 (MH+).

A solution of 44 (0.32 g, 0.5 mmol) and maleic acid (0.2 g, 1.7 mmol) in 25 ml of 90% MeOH was refluxed for 1 h, diluted with ethyl acetate and cooled in an ice-water bath. Pure crystalline product 45 precipitated as a trimaleate salt and was filtered (0.22 g, mp 151–152° C.). CIMS m/z 390 (MH+). Anal. ($C_{20}H_{28}ClN_5O.3C_4H_4O_4$) C, H, N.

Example 8

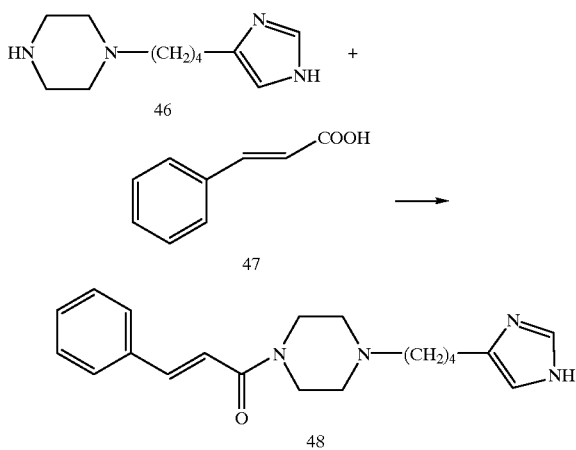

To a stirred suspension of 1.04 g (3.27 mmol) of the trihydrochoride salt of 46 in 40 ml of anhydrous DMF was added portionwise 0.4 g (9.6 mmol) of 60% NaH in oil dispersion, followed by 1 ml of triethylamine, 0.44 g (3.27 mmol) of HOBt, 0.48 g (3.27 mmol) of trans-cinnamic acid 47 and 0.63 g (3.27 mmol) of DEC. The reaction mixture was stirred at room temperature for 2 days, diluted with water, and extracted with $CH_2Cl_2$. Organic solution was concentrated and the residue chromatographed on $SiO_2$ eluting with $CH_2Cl_2$—MeOH-28% $NH_4OH$ (90:9:0.5) to produce 0.32 g (mp 143–145° C.) of the product 48. Cl-MS m/z 339 (MH+).

Example 9

Step 1:

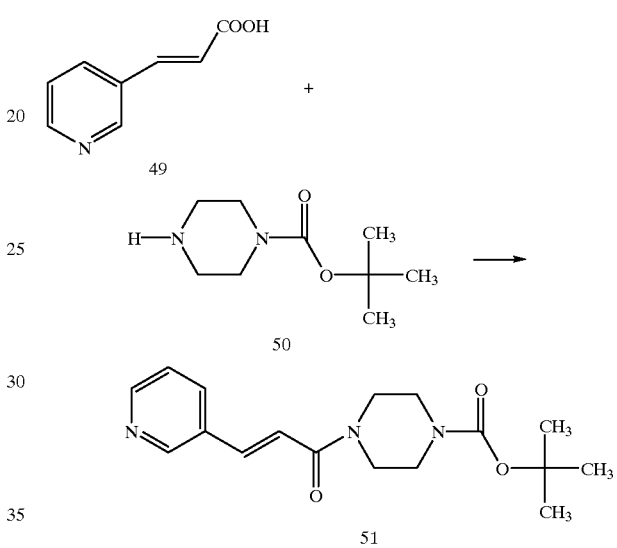

A mixture of trans-3-(3-pyridyl)-acrylic acid 49 (4.01 g, 26.88 mmol), 1-hydroxybenzotriazole (HOBt, 3.63 g, 26.88 mmol), 1-(3-dimethylaminopropyl)-3-ethylcarbodiimide hydrochloride (DEC, 5.15 g, 26.88 mmol), tert-butyl 1-piperazinecarboxylate 50 (5.0 g, 26.88 mmol) and triethylamine (3.7 ml, 26.88 mmol) in 200 ml of anhydrous DMF was stirred at ambient temperature for 24 h, diluted with water, and extracted with $CH_2Cl_2$. Organic solution was washed with $NaHCO_3$, brine, and concentrated. The residue was triturated with hexane and filtered to obtain 7.77 g of the product 51 (mp 174–176° C.). FAB-MS m/z 318 (MH+).

Step 2:

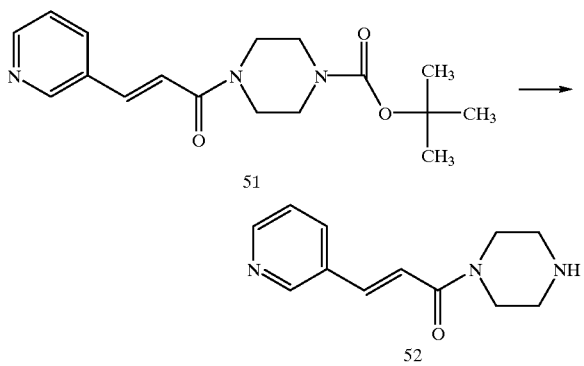

A solution of 51 (1.15 g, 3.6 mmol) in 20 ml of $CH_2Cl_2$ and 3 ml of trifluoroacetic acid was stirred for 18 h, basified with 15% NaOH, and extracted with $CH_2Cl_2$ thoroughly. The organic solution was dried over anhydrous $MgSO_4$, and concentrated. Trituration with ether-hexane (1:2) and filtration of the residue gave 0.34 g (mp 98–100° C.) of the product 52. CI-MS m/z 218 (MH+).

Step 3:

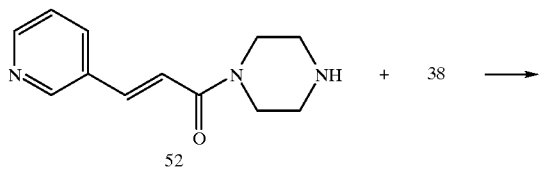

-continued

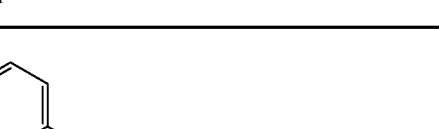

A solution of 38 (0.6 g, 1.58 mmol) in 10 ml of 6M hydrochloric acid and 20 ml of MeOH was stirred at room temperature for 20 h and concentrated to a viscous residue which was mixed with 52 (0.31 g, 1.43 mmol), 3 g of molecular sieve "3A" in 20 ml of 2,2,2-trifluoroethanol, and 0.077 g (1.24 mmol) of sodium cyanoborohydride ($NaCNBH_3$). The mixture was stirred for 20 h at ambient temperature, filtered, and concentrated. The residue was basified with cold 5% NaOH and extracted with $CH_2Cl_2$. The organic solution was concentrated and the residue chromatographed on $SiO_2$ eluting with $CH_2Cl_2$—MeOH-28% $NH_4OH$ (90:10:1) to produce 0.062 g (mp130–133° C.) of the product 53. CI-MS m/z 340 (MH+).

Following the processes described and exemplified above, the compounds listed in Table 1 were prepared:

TABLE 1

| Compound | Mass Spec | $K_i(H_3)$ |
|---|---|---|
| | (CI) 500 (M + 1) | 20 nM |

TABLE 1-continued
| Compound | Mass Spec | $K_i(H_3)$ |
|---|---|---|
| 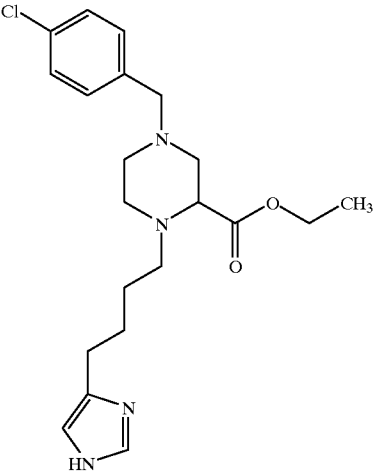 | (FAB) 405 (M + 1) | 26 mM |
| 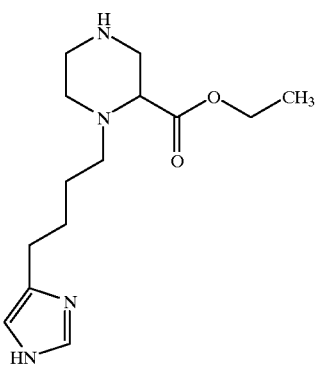 | (CI) 281 (M + 1) | 32 nM |
| 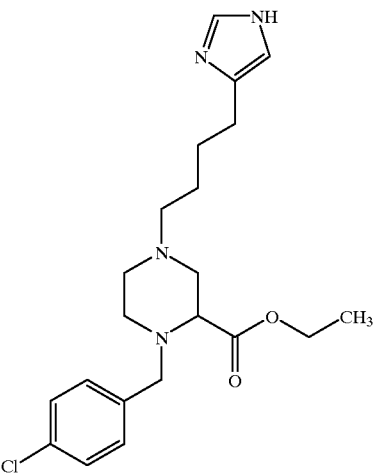 | (FAB) 403 (M + 1) | 46 nM |

TABLE 1-continued
| Compound | Mass Spec | $K_i(H_3)$ |
|---|---|---|
| 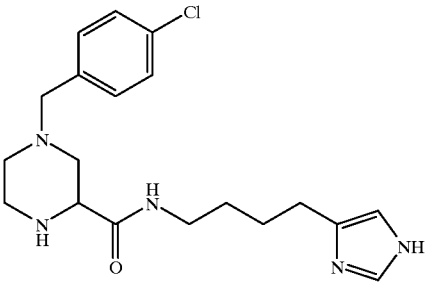 | (CI) 376 (M + 1) | 46 nM |
| 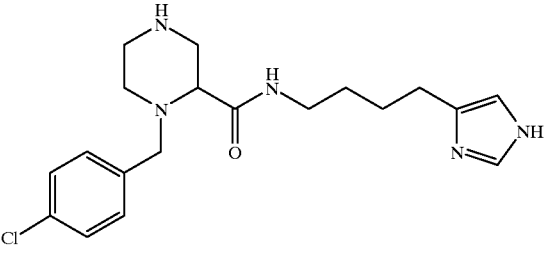 | (FAB) 376 (M + 1) | 38 nM |
| 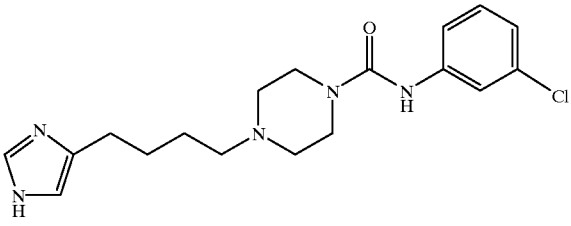 | (FAB) 362 (M + 1) | 6 nM |
| 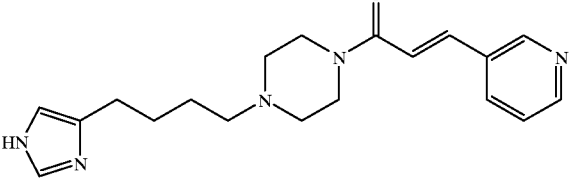 | (FAB) 340 (M + 1) | 25 nM |
| 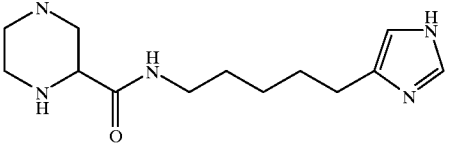 | (CI) 266 (M + 1) | 39 nM |
| 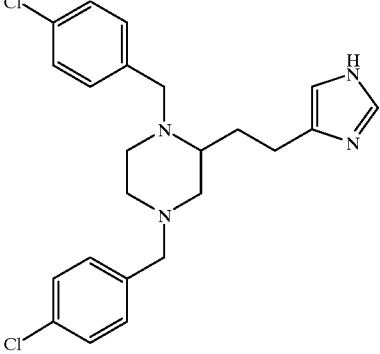 | (FAB) 429 (M + 1) | 45 nM |

TABLE 1-continued
| Compound | Mass Spec | $K_i(H_3)$ |
|---|---|---|
| 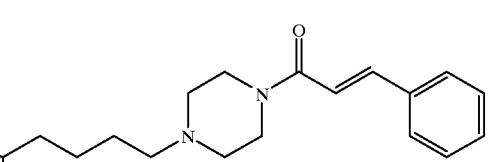 | (CI) 339 (M + 1) | 6 nM |
|  | (CI) 396 (M + 1) | 14 nM |
Table 2 contains a list of additionally prepared compounds belonging to Formula 1.
TABLE 2
| Compound | Mass Spec |
|---|---|
| | (CI) 355 (M + 1) |
| | (FAB) 598 (M + 1) |

TABLE 2-continued

| Compound | Mass Spec |
|---|---|
| (structure: 4-(1H-imidazol-4-ylmethyl)-1-(4-chlorobenzyl)piperazine-2-carboxylic acid ethyl ester) | (EI)<br>362 (M+) |
| (structure: 4-(1H-imidazol-4-ylmethyl)-1-(4-chlorophenylsulfonyl)piperazine-2-carboxylic acid ethyl ester) | (CI)<br>413 (M + 1) |
| (structure: 1-(1H-imidazol-4-ylmethyl)-4-(4-chlorobenzyl)piperazine-2-carboxylic acid ethyl ester) | (CI)<br>363 (M + 1) |
| (structure: 1-(4-chlorobenzyl)-2-[2-(1H-imidazol-4-yl)ethyl]piperazine) | (FAB)<br>305 (M + 1) |

TABLE 2-continued
| Compound | Mass Spec |
|---|---|
| 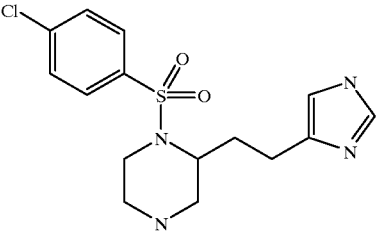 | (FAB) 355 (M + 1) |
| 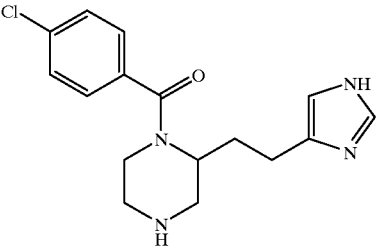 | (FAB) 319 (M + 1) |
| 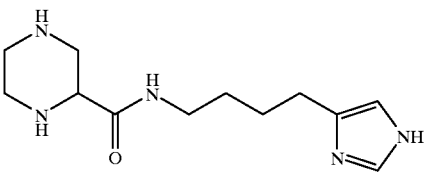 | (CI) 252 (M + 1) |
| 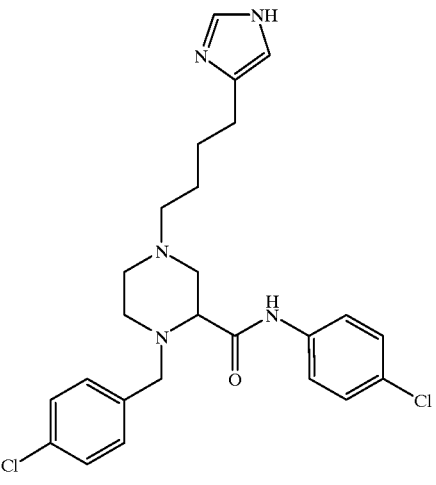 | (FAB) 486 (M + 1) |
| 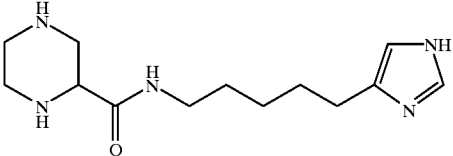 | |

TABLE 2-continued

| Compound | Mass Spec |
|---|---|
| [structure: ethyl piperazine-2-carboxylate with N-CH2-imidazole and N-SO2-(4-chlorophenyl)] | (CI) 413 (M + 1) |
| [structure: ethyl piperazine-2-carboxylate with two N-CH2-imidazole substituents] | (CI) 319 (M + 1) |
| [structure: ethyl piperazine-2-carboxylate with N-CH2-imidazole] | (CI) 239 (M + 1) |
| [structure: ethyl piperazine-2-carboxylate with N-CH2-imidazole and N-C(O)-(4-chlorophenyl)] | (FAB) 377 (M + 1) |

TABLE 2-continued

| Compound | Mass Spec |
|---|---|
| [structure] | (CI)<br>377 (M + 1) |
| [structure] | (CI)<br>457 (M + 1) |
| [structure] | (CI)<br>319 (M + 1) |
| [structure] | (FAB)<br>486 (M + 1) |

TABLE 2-continued
| Compound | Mass Spec |
|---|---|
| 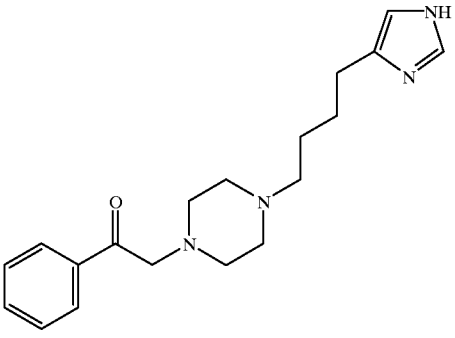 | (FAB)<br>327 (M + 1) |
| 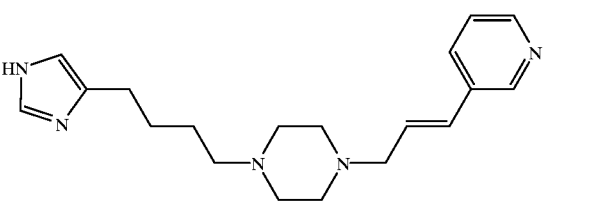 | (FAB)<br>326 (M + 1) |
| 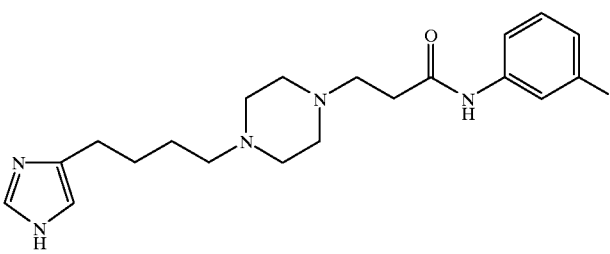 | (CI)<br>390 (M + 1) |
| 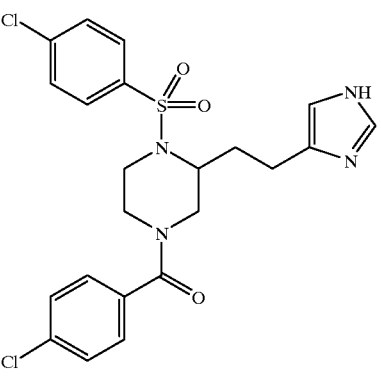 | (CI)<br>493 (M + 1) |
| 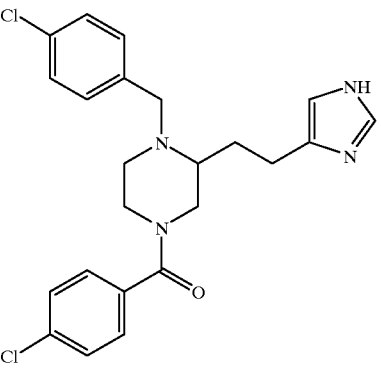 | (CI)<br>443 (M + 1) |

TABLE 2-continued
| Compound | Mass Spec |
|---|---|
| 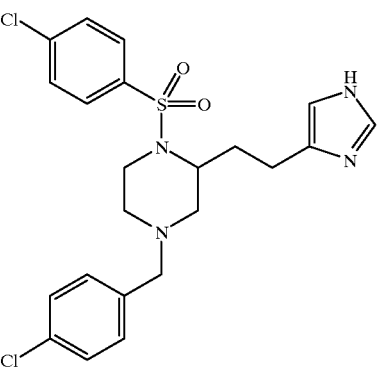 | (CI)<br>479 (M + 1) |
| 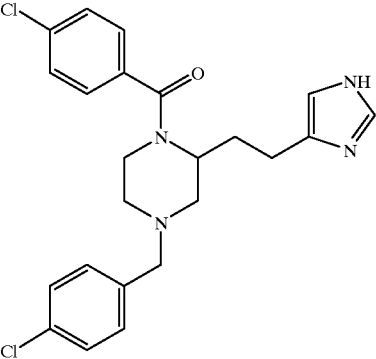 | (CI)<br>443 (M + 1) |
| 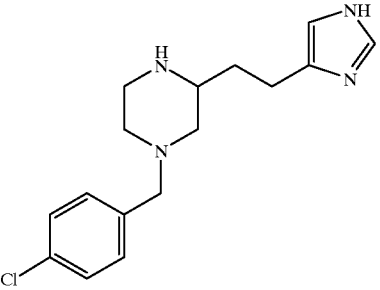 | (FAB)<br>305 (M + 1) |
| 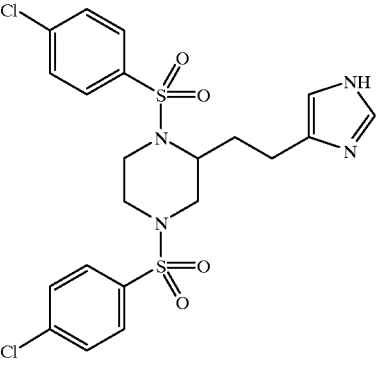 | (FAB)<br>529 (M + 1) |

TABLE 2-continued

| Compound | Mass Spec |
|---|---|
| [structure: 4-chlorobenzoyl-piperazine with imidazole-ethyl and 4-chlorophenylsulfonyl substituents] | (FAB)<br>493 (M + 1) |
| [structure: trans-2,5-dimethylpiperazine with imidazolylmethyl and (3-chloroanilide)propyl substituents] | (FAB)<br>376 (M + 1) |
| [structure: 4-chlorobenzyl-piperazine with imidazole-ethyl and 4-chlorophenylsulfonyl substituents] | (CI)<br>479 (M + 1) |

Procedure for $H_3$ Receptor Binding Assay

The source of the $H_3$ receptors in this experiment was guinea pig brain. The animals used weighed 400–600 g. The tissue was homogenized using a Polytron in a solution of 50 mM Tris, pH 7.5. The final concentration of tissue in the homogenization buffer was 10% w/v. The homogenates were centrifuged at 1000×g for 10 min. in order to remove clumps of tissue and debris. The resulting supernatants were then centrifuged at 50,000×g for 20 min. in order to sediment the membranes, which were next washed 3 times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/mL with 0.1% DMSO. Membranes were then added (400 µg of protein) to the reaction tubes. The reaction was started by the addition of 3 nM [$^3$H]R-α-methylhistamine (8.8 Ci/mmol) or [$^3$H]-N-methylhistamine (80 Ci/mmol) and incubated at 30° C. for 30 min. Bound ligand was separated from unbound ligand by filtration, and the amount of radioactive ligand bound to the membranes was quantitated by liquid scintillation spectrometry. All incubations were performed in duplicate and the standard error was less than 10% in all instances. Compounds that inhibited greater than 70% of the specific binding of radioactive ligand to the receptor were serially diluted to determine a $K_i$ (nM) or % inhibition for $H_3$. The results are given in Table 1.

What is claimed is:

1. A compound selected from the group consisting of the molecules represented by the following chemical structures:

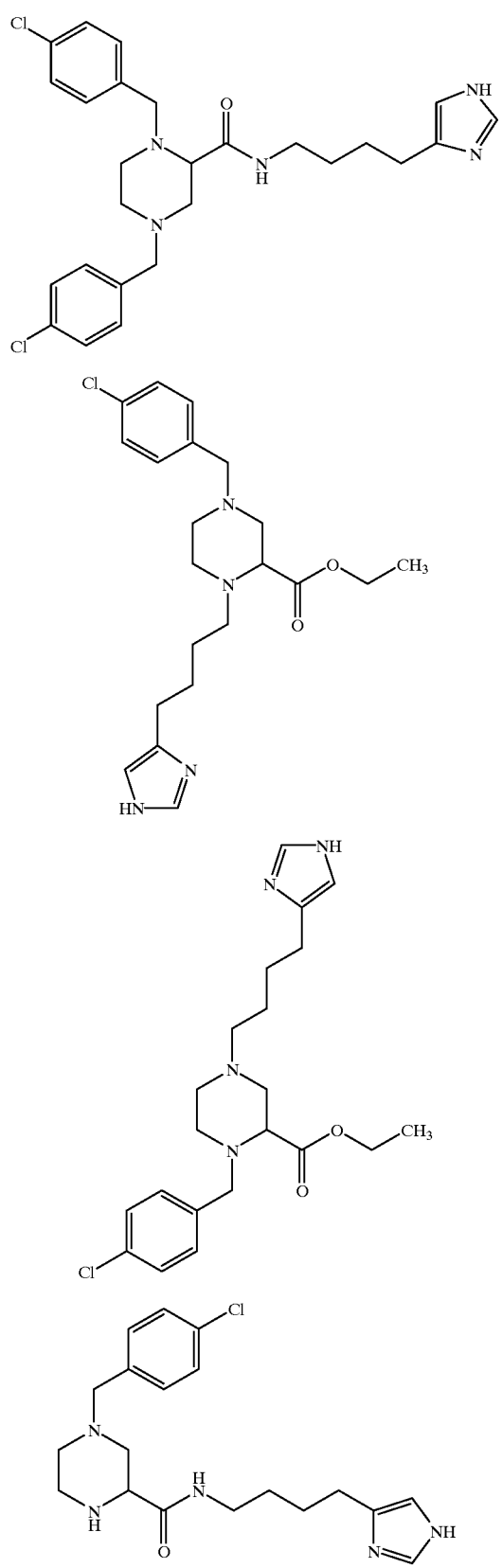
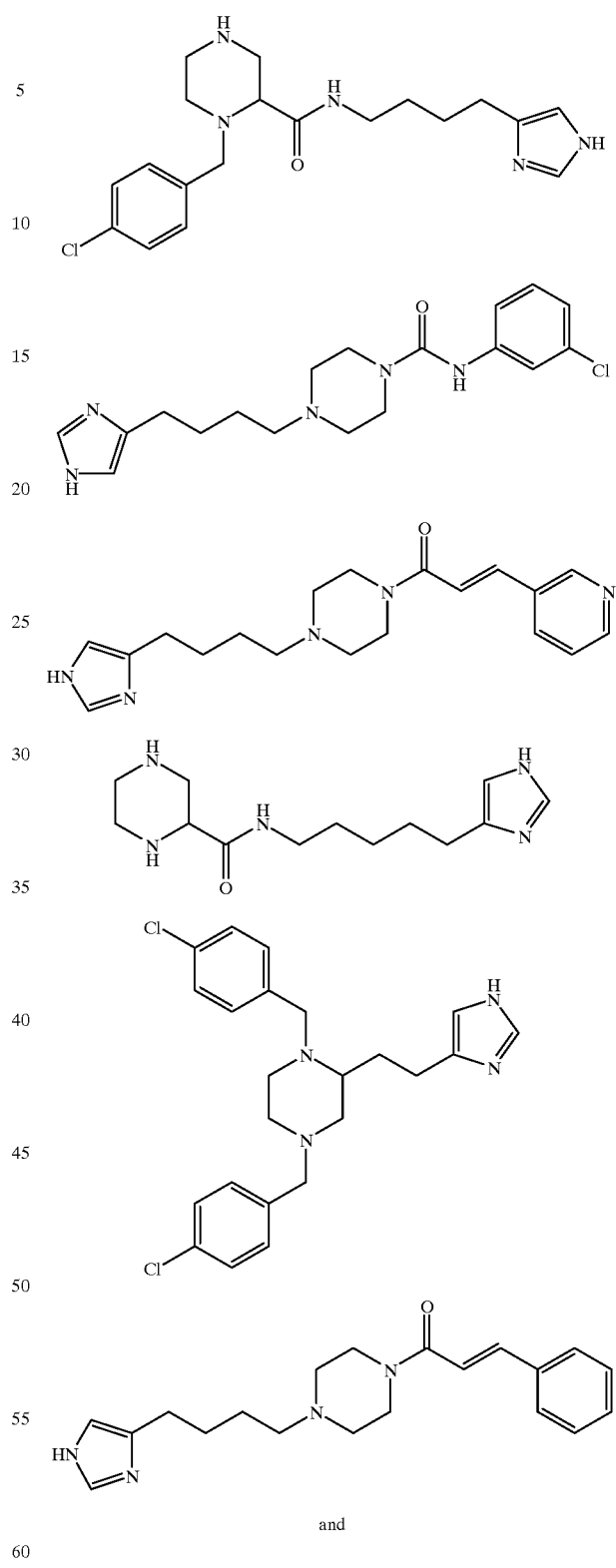
and

-continued
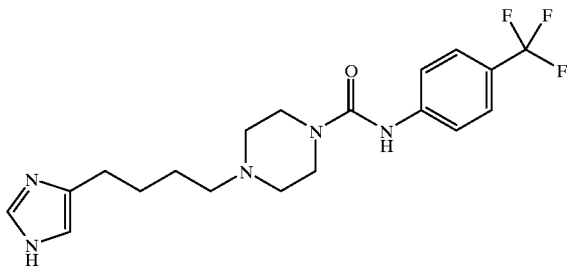
2. A method of preparing a pharmaceutical composition comprising admixing a compound of claim 1 with a pharmaceutically acceptable carrier.
3. A pharmaceutical composition comprising a pharmaceutically acceptable carrier and an effective amount of a compound of claim 1.
* * * * *